(12) United States Patent
Yuge et al.

(10) Patent No.: US 9,494,949 B2
(45) Date of Patent: Nov. 15, 2016

(54) GRAVITY CONTROL DEVICE

(71) Applicants: Space Bio-Laboratories, Ltd., Hiroshima-shi, Hiroshima (JP); iXs Research Corporation, Kawasaki-shi, Kanagawa (JP)

(72) Inventors: Rui Yuge, Hiroshima (JP); Yumi Kawahara, Hiroshima (JP); Fuminori Yamasaki, Kawasaki (JP)

(73) Assignees: SPACE BIO-LABORATORIES CO., LTD., Hiroshima-Shi, Hiroshima (JP); IXS RESEARCH CORPORATION, Kawasaki-Shi, Kanagawa (JP)

( * ) Notice: Subject to any disclaimer, the term of this patent is extended or adjusted under 35 U.S.C. 154(b) by 0 days.

(21) Appl. No.: 14/893,041

(22) PCT Filed: Jun. 13, 2014

(86) PCT No.: PCT/JP2014/065704
§ 371 (c)(1),
(2) Date: Nov. 20, 2015

(87) PCT Pub. No.: WO2014/200084
PCT Pub. Date: Dec. 18, 2014

(65) Prior Publication Data
US 2016/0103454 A1    Apr. 14, 2016

(30) Foreign Application Priority Data
Jun. 13, 2013 (JP) .................... 2013-124777

(51) Int. Cl.
| G01C 19/04 | (2006.01) |
| G05D 13/26 | (2006.01) |
| B64G 7/00  | (2006.01) |
| C12M 3/04  | (2006.01) |
| C12M 1/42  | (2006.01) |
| C12M 1/34  | (2006.01) |
| G05D 13/14 | (2006.01) |

(52) U.S. Cl.
CPC ............. G05D 13/26 (2013.01); B64G 7/00 (2013.01); C12M 27/10 (2013.01); C12M 35/04 (2013.01); C12M 41/40 (2013.01); G05D 13/14 (2013.01)

(58) Field of Classification Search
CPC ............... G01N 2035/00336; Y10S 117/901; G06G 7/22; G01C 21/18
USPC ......................................................... 74/64, 5.4
See application file for complete search history.

(56) References Cited

U.S. PATENT DOCUMENTS

| 3,597,598 A * | 8/1971 | McAllister ............. G01C 21/16 33/318 |
| 2003/0041800 A1* | 3/2003 | Uemura .................... C30B 7/00 117/200 |
| 2003/0159532 A1* | 8/2003 | Adcock ................... F16H 33/10 74/5 R |

FOREIGN PATENT DOCUMENTS

| JP | 2000-079900 | 3/2000 |
| JP | 2007-131261 | 5/2007 |
| JP | 2008-273276 | 11/2008 |
| JP | 2010-193910 | 9/2010 |

* cited by examiner

Primary Examiner — William Kelleher
Assistant Examiner — Jake Cook
(74) Attorney, Agent, or Firm — Howard & Howard Attorneys PLLC

(57) ABSTRACT

The gravity control apparatus (1) comprises: a first rotating body (10) that rotates along a first shaft (11a) as a result of being driven by a first driving device; a second rotating body (20) that rotates along a second shaft that is orthogonal to the first shaft (11a) within the region of rotation of the first rotating body (10) as a result of being driven by a second driving device; an accelerometer (40) that is set at any position on the second rotating body (20) and detects acceleration; and a control device (50) that controls driving by the first driving device and the second driving device. The control device (50) controls driving by the first driving device and the second driving device on the basis of acceleration data detected by the accelerometer (40).

5 Claims, 2 Drawing Sheets

GRAVITY CONTROL DEVICE

CROSS REFERENCE TO RELATED APPLICATIONS

This application is a national stage application of PCT/JP2014/065704, filed Jun. 13, 2014, which claims priority off of Japanese Patent Application Serial No. 2013-124777, filed Jun. 13, 2013, the disclosures of which are hereby incorporated by reference in their entirety.

TECHNICAL FIELD

The present disclosure relates to a gravity control apparatus.

BACKGROUND ART

In various fields, apparatus capable of controlling gravity are proposed. For example, from cell cultivation experiments and/or the like in space, it is known that growth of living things is greatly influenced by gravity, and apparatus have been proposed that change gravity and generate pseudo-microgravity so as to accomplish experiments on cell cultivation in a zero-gravity environment or a low-gravity environment even on the earth.

For example, as disclosed in Patent Literature 1, there is an apparatus comprising a first rotating body that rotates around a first rotation shaft, and a second rotating body that rotates around a second rotation shaft that is orthogonal to the first rotation shaft, and causes a culture vessel to rotate three-dimensionally.

CITATION LIST

Patent Literature

Patent Literature 1: Unexamined Japanese Patent Application Kokai, Publication No. 2010-193910.

SUMMARY OF INVENTION

Technical Problem

In Patent Literature 1, rotation of the first rotating body and the second rotating body is controlled on the basis of complex computation formulas, thus presenting the problem that the manufacturing cost of the apparatus is high.

In consideration of the foregoing, it is a an objective of the present disclosure to provide a gravity control apparatus for which manufacturing costs can be reduced because it is possible to control rotation of the first rotating body and second rotating body with a simple process.

Solution to Problem

The gravity control apparatus according to the present disclosure comprises:

a first rotating body that rotates along a first axis as a result of being driven by a first driving device;

a second rotating body that rotates along a second axis orthogonal to the first axis, within the region of rotation of the first rotating body, as a result of being driven by a second driving device;

an accelerometer that is positioned at any position on the second rotating body and detects acceleration; and a control device that controls driving of the first driving device and the second driving device;

wherein the control device controls driving by the first driving device and the second driving device on the basis of acceleration data detected by the accelerometer.

In addition, the gravity control apparatus according to claim 1, wherein the control device calculates an acceleration vector from Equation 1 below and controls driving by the first driving device and the second driving device so that the integral of the acceleration vector over a prescribed time becomes a prescribed value:

[Formula 1]

$$A = g + r\omega^2 \quad \text{(Equation 1)},$$

where A, g, r, and ω respectively represent an acceleration vector at an arbitrary point P in the second rotating body, a gravitational acceleration vector at the point P, a distance vector from a point of intersection of the first axis and the second axis to the point P, and an angular velocity vector at the point P.

Advantageous Effects of Invention

With the gravity control apparatus according to the present disclosure, it is possible to reduce manufacturing costs because it is possible to control rotation of the first rotating body and second rotating body with a simple process.

DESCRIPTION OF EMBODIMENTS

Figure 1:
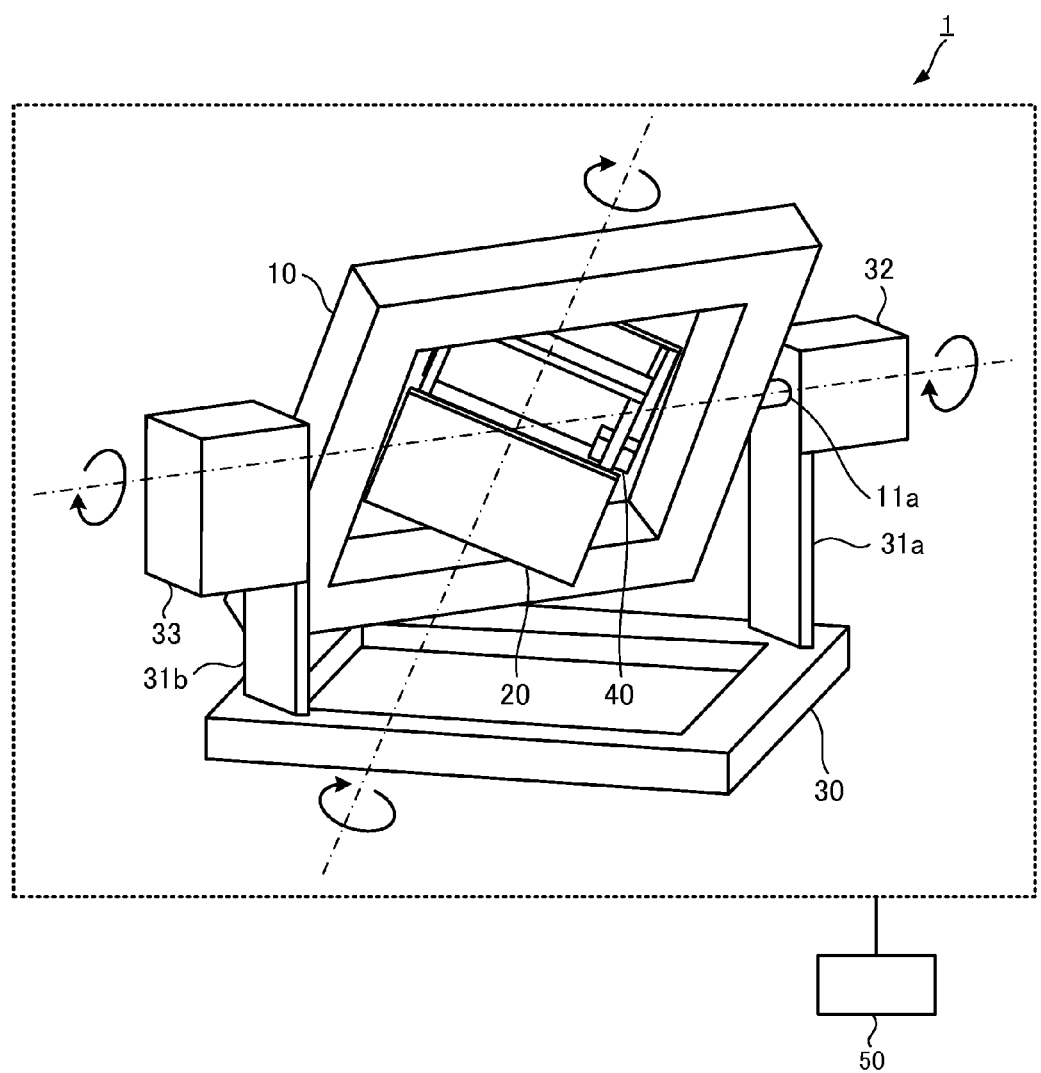
FIG. 1 is an oblique view showing a state in which a gravity control apparatus is operating.
Figure 2:
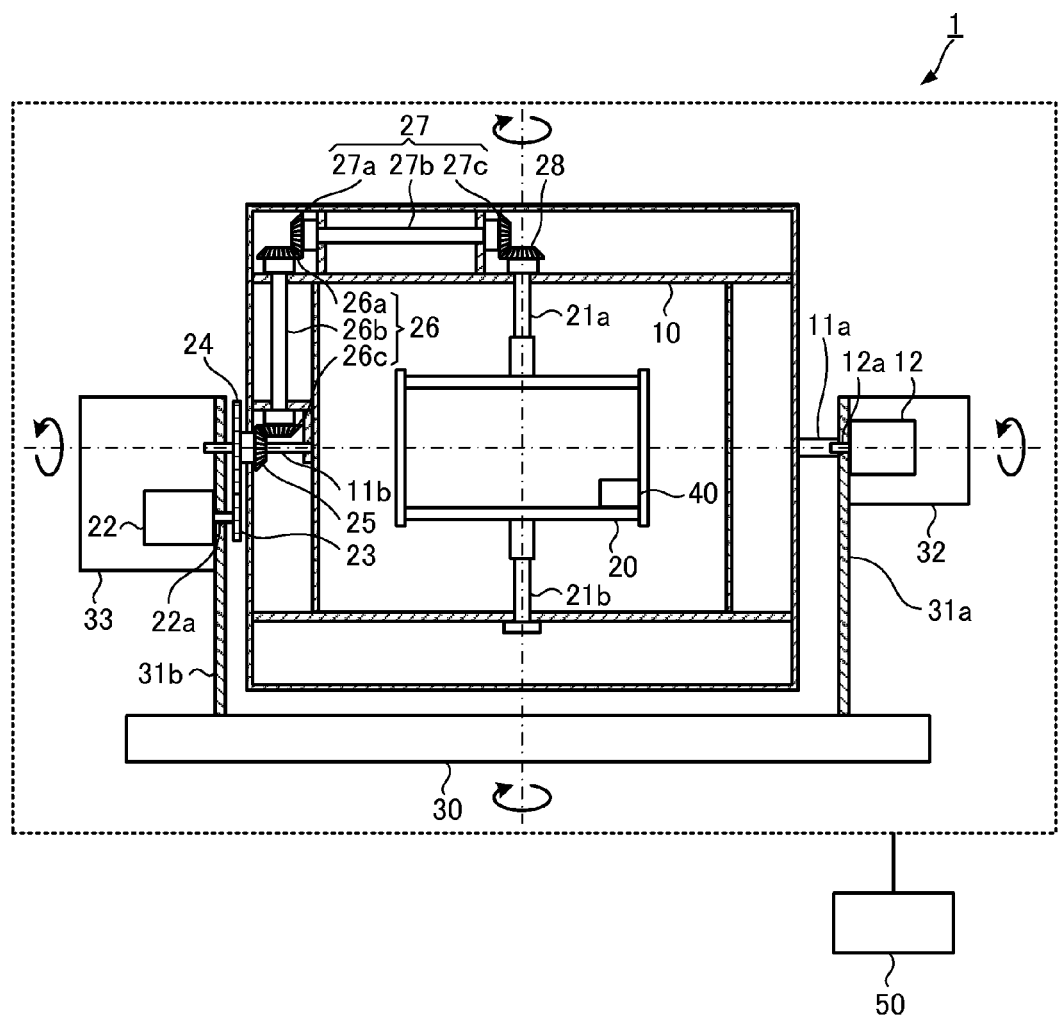
FIG. 2 is a partial cross-sectional view showing an internal structure of a gravity control apparatus.

Below, a gravity control apparatus according to an exemplary embodiment is described with reference to the drawings. A gravity control apparatus 1 comprises a first rotating body 10, first shafts 11a and 11b, a first driving device 12 housed in a first driving device housing unit 32, a second rotating body 20, a second shaft 21a and 21b, a second driving device 22 housed in a second driving device housing unit 33, a support platform 30, support members 31a and 31b, an acceleration detection device 40 and a control device 50, as shown in FIG. 1 and FIG. 2.

The support members 31a and 31b are established opposite each other on the support platform 30. The first rotating body 10, the second rotating body 20 and/or the like are supported between the support members 31a and 31b.

The first rotating body 10 is axially supported on the first shafts 11a and 11b. The first shafts 11a and 11b are positioned coaxially. One end of the first shaft 11a is connected to the first rotating body 10, and in addition, the other end is connected to an output shaft 12a of the first driving device 12. The first shaft 11b may be in a configuration fixed to the support member 31a with the first rotating body 10 in a slidable state, or may be in a configuration fixed to the first rotating body 10 and slidable with respect to the support member 31a. With this structure, when the first driving device 12 drives, the first shaft 11a connected to the output shaft 12a rotates, and the first rotating body 10 rotates around the first shafts 11a and 11b.

The first rotating body 10 here is a rectangular frame, and the second rotating body 20 is placed within and has space to rotate in the inside region of the rotation region of the first rotating body 10.

The second shafts 21a and 21b are respectively attached to facing frames of the first rotating body 10. The second shafts 21a and 21b are positioned coaxially. The second rotating body 20 is attached to the second shafts 21a and 21b.

One end of the second shaft 21a is connected to the second rotating body 20, and in addition, the other end is connected to a bevel gear 28. When the bevel gear 28 rotates, the second rotating body 20 rotates in the inside region of the first rotating body 10. One end of the second shaft 21b is connected to the second rotating body 20, and the other end is slidably attached to the first rotating body 10.

The second rotating body 20 is a place to which various objects to be placed in various gravitational environments, such as microgravity environments or supergravity environments, can be attached. For example, a sealed culture vessel for cell cultivation can be attached to the second rotating body 20, and it is possible to accomplish cell culturing experiments under various gravitational environments, such as microgravity environments or supergravity environments. Attachment of the culture vessel to the second rotating body 20 is fixed using a cord, rubber, fixing hardware and/or the like to an arbitrary location on the second rotating body 20. In addition, an attachment unit for attaching a cell vessel may be formed in the second rotating body 20.

The second driving device 22 is installed on the support member 31a. An output shaft 22a of the second driving device 22 is installed parallel to the first shafts 11a and 11b, and a gear 23 is installed on the output shaft 22a. The gear 23 is installed so as to engage with a gear 24 slidably attached to the first shaft 11b.

The gear 24 is formed integrally with a bevel gear 25 positioned inside the first rotating body 10. The first shaft 11b penetrates the gear 24 and the bevel gear 25, and the gear 24 and the bevel gear 25 are slidably configured with respect to the first shaft 11b.

Inside the first rotating body 10, rotational power transfer members 26 and 27 that transfer drive power from the second driving device 22 to the second shaft 21a are positioned.

The rotational power transfer member 26 comprises bevel gears 26a and 26c respectively attached to the two ends of a shaft 26b. The shaft 26b is slidably positioned in the first rotating body 10, and is positioned orthogonal to the first shaft 11a (parallel to the second shafts 21a and 21b).

On the other hand, the rotational power transfer member 27 comprises bevel gears 27a and 27c respectively attached to the two ends of a shaft 27b. The shaft 27b is slidably positioned in the first rotating body 10 and is positioned parallel to the first shaft 11a (orthogonal to the second shafts 21a and 21b).

The bevel gear 26c of the rotational power transfer member 26 engages with the bevel gear 25 attached to the first shaft 11b. In addition, the bevel gear 26a engages with the bevel gear 27a of the rotational power transfer member 27. In addition, the bevel gear 27c engages with the bevel gear 28 attached to the second shaft 21a connected to the second rotating body 20.

For the first driving device 12 and the second driving device 22, electric driving devices capable of supplying rotational power to the first rotating body 10 and the second rotating body 20, and for example a motor such as a servo motor, a stepping motor and/or the like capable of controlling with high precision rotation of the output shafts 12a and 22a is used.

The acceleration detection device 40 is positioned at an arbitrary position on the second rotating body 20, and detects acceleration of the arbitrary position of the second rotating body 20. As the acceleration detection device 40, a three-axis detection sensor capable of detecting acceleration in the x-axis, y-axis and z-axis directions is used.

The control device 50 controls the number of rotations of the first driving device 12 and the second driving device 22, and controls the number of rotations of the first rotating body 10 and the second rotating body 20.

The control device 50 controls driving of the first driving device 12 and the second driving device 22 on the basis of acceleration data detected by the acceleration detection device 40.

The acceleration detection device 40 and the control device 50 preferably have a configuration capable of communicating acceleration data wirelessly. In this case, the acceleration detection device 40 comprises a wireless transmitter, while the control device 50 comprises a wireless receiver.

In addition, the acceleration detection device 40 preferably has a configuration that comprises an internal storage battery, receives power transmission wirelessly from the outside, and accomplishes detection of acceleration and sending to the control device 50. In this case, the support platform 30 and the support members 31a, 31b and/or the like comprise devices capable of accomplishing power transmission to the acceleration detection device 40 at an arbitrary position. As a method of transmitting power, a commonly known method such as a radio wave method, an electromagnetic induction method, an electromagnetic field resonance method and/or the like can be used.

Next, rotational control of the first rotating body 10 and the second rotating body 20 by the control device 50 is described.

While the first driving device 12 and the second driving device 22 drive and the first rotating body 10 and the second rotating body 20 respectively rotate, the acceleration detection device 40 continuously detects acceleration in the three axial directions.

The acceleration data thus detected is sent to the control device 50. With the control device 50, an acceleration vector is calculated using Equation 1, on the basis of the acceleration data sent. When the location where the acceleration detection device 40 is positioned is point P, the symbols A, g, r and ω in Equation 1 respectively indicate an acceleration vector at point P, a gravitational acceleration vector at point P, a distance vector from the center of the second rotating body (the point of intersection of the first shafts 11a and 11b and the second shafts 21a and 21b) to point P, and an angular velocity vector at point P.

[Formula 2]

$$A = g + r\omega^2 \qquad \text{(Equation 1)}$$

With the acceleration detection device 40, acceleration data in each of the three axial directions is obtained, and in the control device 50, an angular velocity vector ($\omega_1$) around the first shafts 11a and 11b at the point P, an angular velocity vector ($\omega_2$) around the second shafts 21a and 21b and a gravitational acceleration vector (g) undergo component analysis from the acceleration data respectively obtained. In addition, an angular acceleration vector (ω) at the point P is analyzed from the angular velocity vector ($\omega_1$) around the first shafts 11a and 11b at the point P, the angular velocity vector ($\omega_2$) around the second shafts 21a and 21b, and an acceleration vector at the point P is calculated on the basis of Equation 1. The aforementioned analysis can be accomplished by an arbitrary method. In addition, an angular velocity vector ($\omega_1$) around the first shafts 11a and 11b at an arbitrary point and an angular velocity vector (0)2) around the second shafts 21a and 21b may have a configuration based on detection number-of-revolutions detection device, or may have a configuration in which the calculation is from the number of rotations of the first driving device 12 and the second driving device 22.

Furthermore, the acceleration vector at the point P is computed continually while the first rotating body 10 and the second rotating body 20 are rotating and is fed back, and driving of the first driving device 12 and the second driving device 22 is controlled so that the integral of the acceleration vector over a prescribed time (for example, 10 minutes) becomes a pseudo-zero-gravity state (around 1/1000 G). Through this, a pseudo-microgravity environment is created. For example, it would be fine to control the first driving device 12 and the second driving device 22 so that the first rotating body 10 and the second rotating body 20 are each caused to rotate at constant angular velocities with the ratio of the angular velocity of the first rotating body 10 to the angular velocity of the second rotating body 20 a prescribed ratio.

In addition, by the control device 50 controlling the respective rotations of the first rotating body 10 and the second rotating body 20 so that the integral of the acceleration vector at the point P over a prescribed time becomes 1/6 G, it is possible to reproduce the gravitational environment on the moon, and it is possible to virtually reproduce various gravitational environments, such as supergravity environments exceeding 1 G, such as 2 G, 3 G and/or the like.

In this manner, with the gravity control apparatus 1 according to the exemplary embodiment, it is possible to create a microgravity environment in a space inside the second rotating body 20 with an easy process and to create various gravitational environments, and it is possible to reduce the cost of the gravity control apparatus 1.

Above, the explanation used an example in which the second driving device 22 is positioned external to the first rotating body 10, but it is similarly possible to accomplish control even with a configuration in which the second driving device 22 is installed on the first rotating body 10 and the second driving device 22 is driven by supplying electric power by a contract-type power supply mechanism such as a coupling comprising a slip ring and a brush, and/or the like.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2013-124777, filed on Jun. 13, 2013, the entire disclosure of which is incorporated by reference herein.

REFERENCE SIGNS LIST

1 Gravity control apparatus
10 First rotating body
11a, 11b First shaft
12 First driving device
12a Output shaft
20 Second rotating body
21a, 21b Second shaft
22 Second driving device
22a Output shaft
23 Gear
24 Gear
25 Bevel gear
26 Rotational power transfer member
26a Bevel gear
26b Shaft
26c Bevel gear
27 Rotational power transfer member
27a Bevel gear
27b Shaft
27c Bevel gear
28 Bevel gear
30 Support platform
31a, 31b Support member
32 First driving device housing unit
33 Second driving device housing unit
40 Acceleration detection device
50 Control device

The invention claimed is:

1. A gravity control apparatus, comprising:
a first rotating body that rotates along a first axis as a result of being driven by a first driving device;
a second rotating body that rotates along a second axis orthogonal to the first axis, within an inside region of the first rotating body, as a result of being driven by a second driving device;
an accelerometer that is positioned at any position on the second rotating body and detects acceleration; and
a control device that controls driving of the first driving device and the second driving device;
wherein the control device calculates an acceleration vector from Equation 1 below and controls driving of the first driving device and the second driving device on the basis of acceleration data detected by the accelerometer so that the integral of teh accelaration vector over a prescribed time becomes a prescribed value:

[Equation 1]

$$A = g + r\omega^2 \quad \text{(Equation 1)},$$

where A, g, r, and $\omega$ respectively represent an acceleration vector at an arbitrary point P in the second rotating body, a gravitational acceleration vector at the point P, a distance vector from a point of intersection of the first axis and the second axis to the point P, and an angular velocity vector at the point P.

2. The gravity control apparatus according to claim 1, further comprising:
a rotational power transfer member that is positioned in the first rotating body and transfers drive power from the second driving device to the second axis,
wherein the first driving device and the second driving device are positioned at an exterior of the region of rotation of the first rotating body, and the rotational power transfer member changes an axial direction of a rotation axis and transfers the drive power from the second driving device to the second axis.

3. The gravity control apparatus according to claim 2, wherein the rotational power transfer member is positioned inside the first rotating body.

4. The gravity control apparatus according to claim 2, wherein the rotational power transfer member includes a bevel gear, and the bevel gear changes the axial direction of the rotation axis.

5. The gravity control apparatus according to claim 2 further comprising,
- another rotational power transfer member that is positioned in the first rotating body and transfers drive power from the second driving device to the second axis, the another rotational power transfer member coupled to the rotational power transfer member,
- wherein the axial direction of the rotation axis of the second driving device is changed three times by the rotational power transfer members on a plane that rotates along the first axis so that the second rotating body rotates, each rotational power transfer member including two bevel gears one on each end.

* * * * *

UNITED STATES PATENT AND TRADEMARK OFFICE
CERTIFICATE OF CORRECTION

PATENT NO. : 9,494,949 B2  
APPLICATION NO. : 14/893041  
DATED : November 15, 2016  
INVENTOR(S) : Rui Yuge et al.

Page 1 of 1

It is certified that error appears in the above-identified patent and that said Letters Patent is hereby corrected as shown below:

On the Title Page

At (71) Applicants:
Please delete "Space Bio-Laboratories, Ltd." and replace with -- Space Bio-Laboratories Co., Ltd. --

Signed and Sealed this
Eighteenth Day of April, 2017

Michelle K. Lee
*Director of the United States Patent and Trademark Office*